US00PP07918P

United States Patent [19]

Bradford et al.

[11] Patent Number: Plant 7,918

[45] Date of Patent: Jul. 21, 1992

[54] NECTARINE TREE (RUBY DIAMOND)

[76] Inventors: Lowell G. Bradford, 12439 E. Savana Rd.; Norman G. Bradford, 11875 E. Savana Rd., both of Le Grand, Calif. 95333

[21] Appl. No.: 650,248

[22] Filed: Feb. 4, 1991

[51] Int. Cl.[5] ..... A01H 5/00

[52] U.S. Cl. ..... Plt./41.3

[58] Field of Search ..... Plt./41

[56] References Cited

U.S. PATENT DOCUMENTS

P.P. 2,879 4/1969 Anderson ..... Plt. 41

P.P. 3,165 5/1972 Anderson ..... Plt. 41

*Primary Examiner*—James R. Feyrer

[57] ABSTRACT

The present invention relates to a nectarine tree and more particularly to a new and distinct variety broadly characterized by a large size, vigorous, hardy, productive and regular bearing tree. The fruit matures under the ecological conditions described approximately the first week in July, with first picking on Jul. 4, 1990. The fruit is uniformly large in size, excellent in flavor, attractively globose in shape, freestone in type, very firm in texture, and full red in skin color. The variety was developed as a hybridized seedling from the selected seed parent of Red Diamond Nectarine (U.S. Plant Pat. No. 3,165), and an unnamed nectarine seedling as the selected pollen parent.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of nectarine tree, which has been denominated varietally as "Ruby Diamond". The present variety was hybridized in 1983 by use in a cultivated area of our experimental orchard at Bradford Farms near Le Grand, Calif., in Merced County (San Joaquin Valley). It was the result of a seedling using Red Diamond Nectarine (U.S. Plant Pat. No. 3,165) as the selected seed parent and an unnamed nectarine seedling as the selected pollen parent. Subsequent to origination of the present variety of nectarine tree, we asexually reproduced it by budding and grafting, and such reproduction of plant and fruit characteristics were true to the original plant in all respects.

The fruit produced by the present variety is similar to that of the Summer Grand Nectarine (U.S. Plant Pat. No. 2,879) by maturing in July, by being very productive, and by being freestone in type, but is distinguished therefrom and an improvemnent thereon by producing fruit that ripens 6 days earlier and is full red in skin color over the entire fruit surface.

The present variety is similar to its selected seed parent, the Red Diamond (U.S. Plant Pat. No. 3,165), in fruit appearance by being a full red colored freestone nectarine with excellent firmness, but is distinguished therefrom and an improvement thereon by producing fruit that ripens 6 days later, is somewhat larger in size, is more globose in shape, and is sweeter in flavor, and by having a large blossom instead of a small blossom.

DRAWING

The accompanying photograph exhibits four whole fruits positioned to display the characteristics of the skin color and form, one fruit divided around the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of hard eating ripe on Jul. 12, 1990. All major color code designations are by reference to the Inter-Society Color Council, National Bureau of Standards. Common color names are also used occasionally.

TREE

Size: Large.
Vigor: Vigorous.
Growth: Spreading and dense.
Form: Vase formed.
Hardiness: Hardy.
Production: Very productive.
Bearing: Regular bearer.
Trunk:
- *Size.*—Medium.
- *Texture.*—Medium.
- *Bark color.*—Dark grayish yellowish brown [81. d.gy.yBr].
- *Lenticles.*—Numerous. Color: Light yellowish brown [76.1.yBr]. Size: ⅛ to ⅜, [3.2-9.5 mm.].

Branches:
- *Size.*—Medium.
- *Texture.*—Medium.
- *Color.*—1st year wood topside: Grayish red [19. gy.R]. 1st year wood underside: Brilliant yellow green [116. brill.YG]. Older wood: Deep yellowish brown [75. deep yBr].
- *Lenticels.*—Numerous, very small.

Leaves:
- *Size.*—Large. Average length: 6"[152.4 mm.]. Average width: 1½" [38.1 mm.].
- *Thickness.*—Medium.
- *Form.*—Elliptical.
- *Apex.*—Acuminate.

*Base.*—Acute.
*Surface.*—Smooth.
*Color.*—Dorsal surface: Moderate olive green [125. OlG]. Ventral surface: Moderate yellow green [120. mYG].
*Margin.*—Finely serrate.
*Venation.*—Pinnately net veined.
*Petiole.*—Average length: 7/16" [11.1 mm.]. Average thickness: 1/16"[1.6 mm.]. Dorsal color: Moderate yellow green [120. m.YG]. Ventral color: Light yellow green [119. l.YG].
*Stipules.*—Numerous. Length: 3/16" to ⅜" [4.8-9.5 mm.].
*Glands.*—Numbers: 2, 3, or 4 per leaf. Position: Mostly oppositely positioned on petiole and base of blade, with a few singles. Size: Medium. Form: Reniform. Color: Moderate yellow green [120. m.YG].

Flower buds:
*Hardiness.*—Hardy.
*Size.*—Medium.
*Length.*—Medium.
*Form.*—Free.
*Surface.*—Pubescent.

Flowers:
*Blooming period.*—Medium as comapred with other varieties.
*Size.*—Large.
*Color.*—Light pink [4. l.Pk].

FRUIT

Maturity when described: Firm and eating ripe, Jul. 12, 1990.
Date of first picking: Jul. 4, 1990.
Date of last picking: Jul. 20, 1990.
Size: Uniform, large.
*Average diameter axially.*—2 9/16" [65.1 mm.].
*Average traversely in suture plane.*—2 9/16" [65.1 mm.].
Form: Uniform, very symmetrical, globose with some slight truncation at the base.
*Longitudinal section form.*—Round.
*Transverse section through diameter.*—Round.
Suture: An inconspicuous shallow line extending from the base to the apex, becoming deeper toward the apex.
Ventral surface: Rounded, lipped very slightly throughout on one side.
Lips: Slightly unequal.
Cavity: Flaring, circular, suture showing on one side only.
*Depth.*—⅜" [9.5 mm.].
*Breadth.*—⅞ "[22.2 mm.].
Base: Slightly truncate, with stem markings typical.
Apex: Rounded.
Pistil point: Some apical and some oblique, very short in length.
Stem: Medium.
*Average length.*—⅜" [9.5 mm.].
*Average width.*—5/32" [4.0 mm.].
Skin:
*Thickness.*—Medium.
*Texture.*—Medium.
*Tenacity.*—Tenacious to flesh.
*Tendency to crack.*—None observed as of yet.
*Color.*—Deep red [13. deep R] over the entire surface with some very small grayish reddish orange [39. gy.rO] freckling near the apex end.

Flesh:

*Color.*—Brilliant orange yellow [67. brill.OY] with some moderate red [15. m.R] streaking near the stone.
*Surface of pit cavity.*—Covered with moderate red [15. m.R] fibers.
*Amygdalin.*—Moderate.
*Juice.*—Abundant, rich.
*Texture.*—Very firm, tough, crisp.
*Fibers.*—Abundant, fine.
*Ripens.*—Evenly.
*Flavor.*—A tasty blend of acid and sugar.
*Aroma.*—Slight.
*Eating quality.*—Best.

STONE

Type: Freestone.
Form: Oval to oblong.
Base: Straight.
Apex: Acute to acuminate.
Sides: Equal.
Surface: Irregularly furrowed toward the ventral edge and pitted toward the base and dorsal fin.
Ridges: Jagged toward the base.
Color: Light brown [57. l.Br
Pit wall: 3/16" [4.8 mm.] thick.
Tendency to split: None observed.
Kernel:
*Form.*—Oval.
*Taste.*—Sweet.
*Viable.*—Yes.
*Average width.*—½" [12.7 mm.].
*Average length.*—¾" [19.1 mm.].
*Color.*—Pale yellow [89. p.Y] when first cracked.
*Pellicle color.*—Dark grayish yellow [91. d.gy.Y].
*Amygdalin.*—Scant.

USE

Market: Fresh and long distance shipping.
Keeping quality: Excellent.
Shipping quality: Excellent.
Resistant to insects: No unusal susceptibilities noted.
Resistance to diseases: No unusual susceptibilities noted.

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of nectarine tree, substantially as illustrated and described, which is similar to its seed parent, Red Diamond (U.S. Plant Pat. No. 3,165), by producing freestone nectarines that are full red in skin color and very firm in texture, but is distinguished therefrom and an improvement thereon by producing fruit that ripens 6 days later, is somewhat larger in size, is more globose in shape, and is sweeter in flavor, and by having a large blossom instead of a small blossom, and which is also similar to the Summer Grand Nectarine (U.S. Plant Pat. No. 2,879) by being very productive and by producing freestone nectarines that mature in July, but is distinguished therefrom and an improvement thereon by producing fruit that ripens 6 days earlier and is full red in skin color over the entire fruit surface.

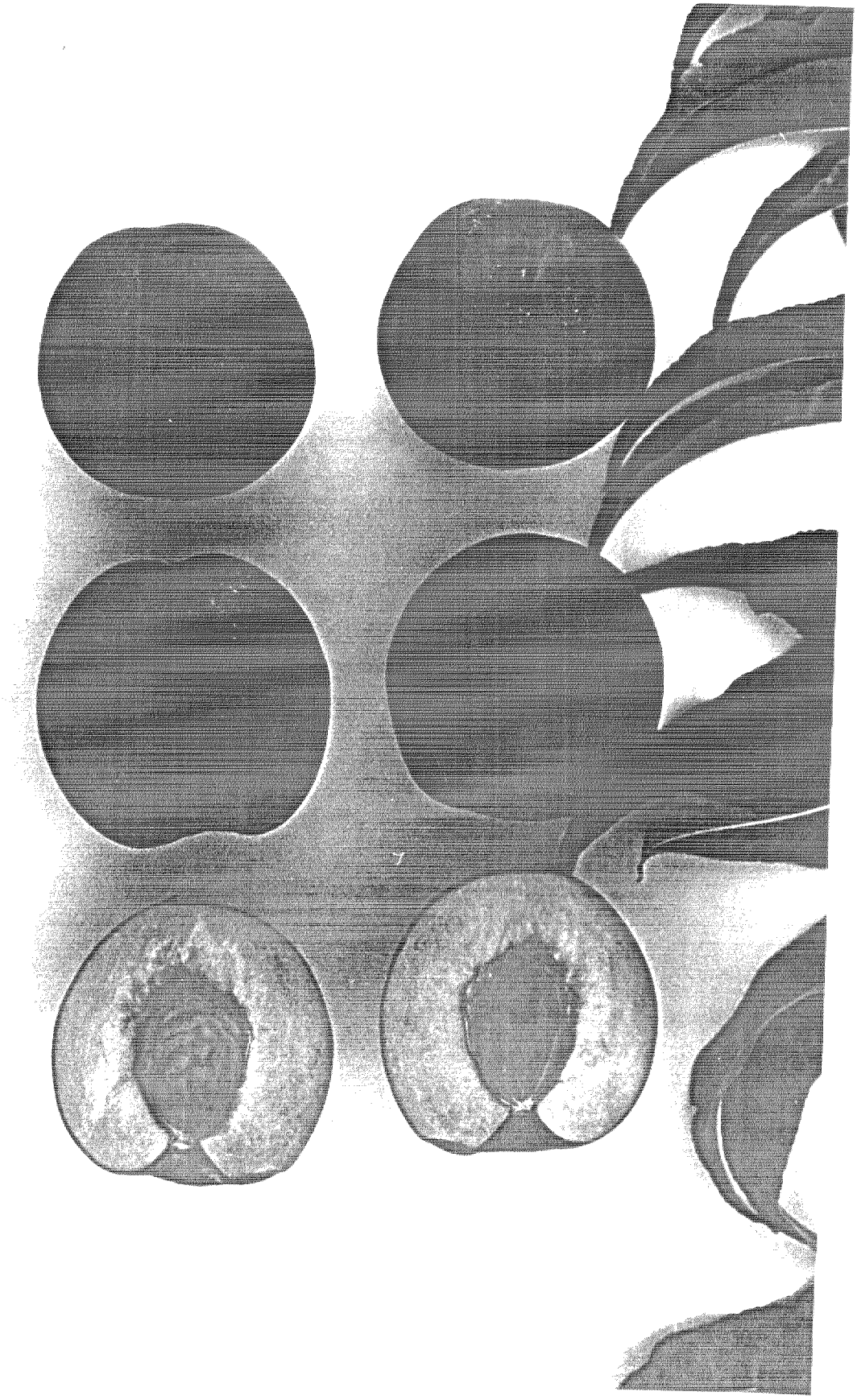

* * * * *